United States Patent [19]

Kimble et al.

[11] 4,200,399
[45] Apr. 29, 1980

[54] RESONANT OPTOACOUSTIC SPECTROSCOPY APPARATUS

[75] Inventors: Harry J. Kimble, Royal Oak; David M. Roessler, Madison Heights, both of Mich.

[73] Assignee: General Motors Corporation, Detroit, Mich.

[21] Appl. No.: 961,994

[22] Filed: Nov. 20, 1978

[51] Int. Cl.² .................... G01J 3/42; G01N 21/22
[52] U.S. Cl. ................................. 356/437; 73/24; 356/440
[58] Field of Search ............... 356/437, 439, 440; 250/343, 345, 351; 73/24

[56] References Cited

U.S. PATENT DOCUMENTS

| | | | |
|---|---|---|---|
| 3,820,901 | 6/1974 | Kreuzer | 250/345 |
| 3,938,365 | 2/1976 | Dewey | 73/24 |
| 3,948,345 | 4/1976 | Rosencwaig | 73/24 |
| 4,028,932 | 6/1977 | Rosencwaig | 73/24 |

Primary Examiner—John K. Corbin
Assistant Examiner—R. A. Rosenberger
Attorney, Agent, or Firm—Warren D. Hill

[57] ABSTRACT

Resonant optoacoustic cells are used in measurements of the concentration and composition of a gas or aerosol. Such apparatus is improved by providing a small absorption cell acoustically coupled to a resonant acoustic cavity so that the time delay associated with the flow of a gas or aerosol through the absorption cell is greatly reduced.

1 Claim, 3 Drawing Figures

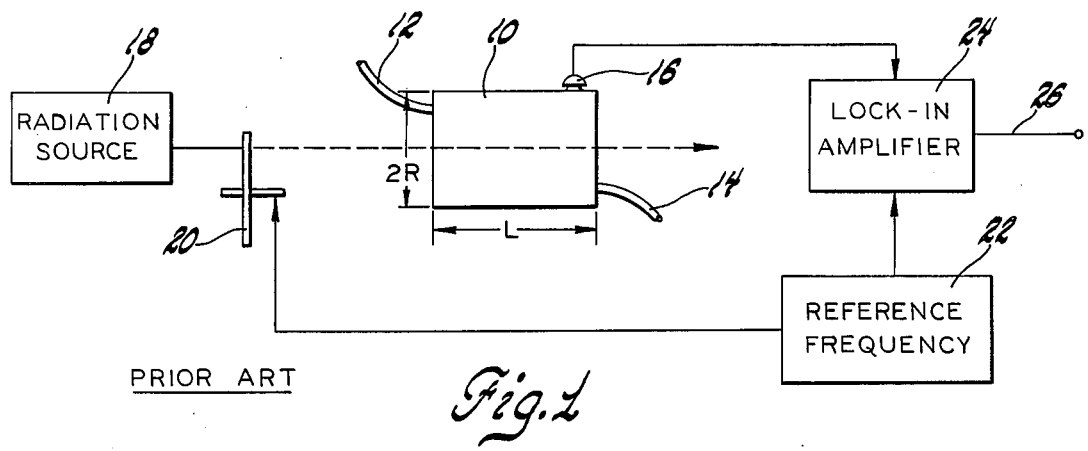
PRIOR ART *Fig. 1*
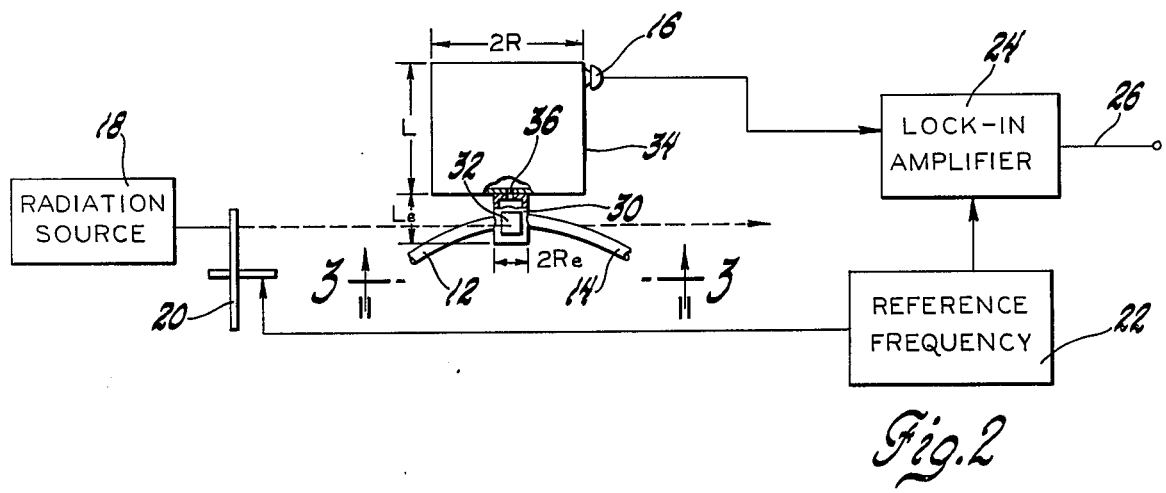
*Fig. 2*
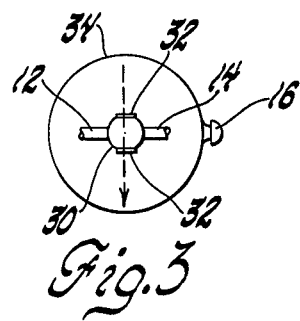
*Fig. 3*

RESONANT OPTOACOUSTIC SPECTROSCOPY APPARATUS

This invention relates to a resonant optoacoustic spectroscopy apparatus for measurement of gas or aerosols. In particular, the invention is directed to such apparatus for use in flowing systems.

It has been known to use resonant optoacoustic cells wherein a sample chamber containing the gas or aerosol being measured is of such porportions that it causes a fundamental acoustic resonance at the frequency at which pulses of radiation are applied. Physical and instrumental constraints limit a practical system to acoustic resonant frequencies below about 10 kilohertz thereby setting a lower limit for the dimensions of the resonant cell. The large volume of such a resonant cell requires a substantial time for replacement of the gas therein so that where measurements are being made of flowing gas a long time delay is required for flow of a fresh sample of gas into the chamber.

It is, therefore, a general object of the invention to provide a resonant optoacoustic spectroscopy system wherein a fast time response to changes in a flowing gas is obtained. It is a further object in such a system to provide a resonant optoacoustic device in which the size of the absorption cell is not restricted by the limitations on the fundamental acoustic resonance of the system.

The invention is carried out by providing in an optoacoustic apparatus a resonant acoustic cavity dimensioned to provide the desired fundamental frequency and an absorption cell acoustically coupled to the resonant acoustic cavity to excite an acoustic resonance of the cavity, the volume of the absorption cell being small enough to allow a fast response time to changes in a flowing gas.

The above and other advantages will be made more apparent from the following specification taken in conjunction with the accompanying drawings wherein like reference numerals refer to like parts and wherein:

FIG. 1 is a schematic view of an optoacoustic spectroscopy system as practiced prior to this invention, FIG. 2 is a schematic diagram of an optoacoustic spectroscopy system having an acoustic cavity separate from the absorption cell according to the invention, and FIG. 3 is a view of the absorption cell taken along line 3—3 of FIG. 2.

The prior art of optoacoustic spectroscopy is represented by the system shown in FIG. 1. A conventional resonant optoacoustic cell comprises a cylindrical cavity 10 of diameter 2R and length L. Gas is admitted and exhausted from the cavity by a flow input 12 and output 14 respectively. A microphone 16 mounted on a wall of the cell 10 responds to pressure variations in the cavity. A radiation source 18, preferably a laser, provides a beam of light which is passed through the cell 10. The light has a wavelength which is selectively absorbed by the specific gas or aerosol being measured. A mechanical chopper 20 between the source 18 and cell 10 interrupts the radiation beam at a frequency equal to the fundamental resonant frequency of the cell 10. A reference frequency source 22 which is tuned to a resonant frequency of the cell 10 controls the speed of the chopper 20 and also provides a reference signal to a lock-in amplifier 24. The lock-in amplifier receives the output from the microphone 16 and produces a signal on an output line 26 which is the microphone output signal having the same modulation frequency as the reference frequency 22. A representative lock-in amplifier is model 124A manufactured by Princeton Applied Research Corp., Princeton, N.J. The lock-in amplifier multiplies the microphone signal and the reference signal and time-averages the product. All the signal frequencies not the same as the reference frequency cancel out. The amplifier output signal contains only that microphone signal which is synchronous with the reference signal.

In operation the absorption cell 10 is charged with a gas or aerosol the composition and concentration of which is to be measured. Light from the radiation source 18 is absorbed by the gas or aerosol according to its composition and concentration thereby heating the contents of the absorption cell to cause a pressure rise. Since the radiation beam is modulated at the resonant frequency of the absorption cell, the consequent pressure oscillations in the contents of the cell excite the cell at its fundamental acoustic resonance and the amplitude of the pressure waves as recorded by the microphone is proportional to the degree of absorption by the gas or aerosol. In consequence, the output of the lock-in amplifer 24 is a measure of the composition and concentration of the gas or aerosol in the absorption cell 10.

The dimensions R and L of such an absorption cell are normally chosen to be in the range of 5 to 10 centimeters so that the fundamental acoustic resonance of the cavity is below 10 kilohertz. This upper limit is set by requiring that the period of the fundamental resonance be long compared to the relaxation time for transferring the absorbed optical energy into translational energy. In addition, modulation of the incident radiation and detection of the acoustic signals becomes more difficult at frequencies above 10 kilohertz. The lower limit for the dimensions of the resonant cell establishes a cell volume of several hundred cubic centimeters. The time constant t required for a change of the cell contents is limited to a value $t = V/f$ for a cell of volume V and a flow rate of a gas f. Thus, for V equal to 1,000 cubic centimeters and f equal to 100 cubic centimeters per second, for example, the response time t to changes in the flow is 10 seconds. With such a system, a rapid response to changes in a gas flowing through an absorption cell is not possible.

The system according to the invention revealed in FIG. 2 of the drawings provides a fast response time to changes in the gas flow while maintaining a high sensitivity. Most of the elements of the system in FIG. 2 remain the same as those in FIG. 1. The common elements include the microphone 16, the radiation source 18, the chopper 20, the reference frequency source 22 and amplifier 24 having its output line 26. In place of the cell 10, however, there is provided a small absorption cell 30 comprising a cylindrical chamber of radius $R_e$ and a length $L_e$. Flow input lines 12 and 14 are connected to the sides of the cell 30 to pass a flowing gas or aerosol through the cell. The light beam from the radiation source also passes through the cell. As shown in the end view of the absorption cell depicted in FIG. 3, a pair of windows 32 arranged so as not to interfere with the inlet and output lines is provided to allow the passage of the exciting radiation. The absorption cell 30 is coupled to an end of a separate resonant acoustic cavity 34. The acoustic cavity 34 has dimensions much larger than the absorption cell and preferably have a radius R and length L, the same as that of the FIG. 1 cavity. The absorption cell is coupled to the acoustic cavity through an opening 36 which may be uncovered as shown or which may be covered by a thin membrane or diaphragm which readily transmits the pressure variations produced in the absorption cell to the acoustic cavity where an acoustic resonance of the large volume is excited.

The resonant cavity 34 designed for a lowest order longitudinal resonance of 1,700 hertz would have dimensions on the order of $R=5$ cm and $L=10$ cm. An absorption cell 30 coupled to that cavity would preferably have dimensions $R_e=1$ cm and $L_e=0.5$ cm. The absorption cell then would have a volume of about 1.5 cubic centimeters and if a gas flow of 100 cubic centimeters per second is provided, the time constant t will equal 15 milliseconds to provide a fast response time to changes in the gas flow. The remainder of the system of FIG. 2 preferably comprises a radiation source 18 having an output wavelength for which the sample has appreciable absorption. For example, a one watt argon ion laser having an output wavelength of 5,145 Å is suitable for nitrogen dioxide. The reference frequency and chopper frequency is 1,700 hertz to match the resonant frequency of the acoustic cavity. The microphone 16 is an electret microphone model BT-1759 manufactured by Knowles Electronics, Inc. of Franklin Park, Ill. The coupling coefficient between the absorption chamber and the resonant cavity is approximately 10%. If it is desired to cover the aperture 36 with a diaphragm, a preferred diaphragm material is a mylar film. In the case where a diaphragm is used, the resonant cavity can be filled with a special gas, for example xenon, to provide a factor of 2 or 3 gain in sensitivity.

It can be shown that the ratio of pressure amplitudes for the excitation of the fundamental longitudinal resonance for the cells of FIG. 1 and 2 is proportional to the ratio of the radii of the absorption cells. This calculated pressure amplitude ratio relies on the assumption that the small cavity in FIG. 2 represents a negligible perturbation to the quality factor Q and eigenfunctions of the large cavity and that the geometry of the small cavity does not hinder the transference of energy to the acoustic resonance of the large volume. Thus, if the absorption cell of FIG. 1 has the dimensions $R=5$ cm and $L=10$ cm and the dimensions for the absorption cell of FIG. 2 are $R_E=1$ cm and $L_E=0.5$ cm, then the pressure amplitude of the FIG. 2 apparatus will be less by a factor of 5 and thus has only a slight disadvantage. On the other hand, the ratio of the volume of the two absorption cells and, therefore, the time constants is 500 to 1. Thus, the smaller volume greatly enhances the sensitivity to changes in a flowing gas.

It will thus be seen that the optoacoustic cell according to this invention produces signals generally comparable to those for the more conventional arrangement of the prior art while providing a significant reduction in the response time of measurements in flowing systems.

The embodiments of the invention in which an exclusive property or privilege is claimed are defined as follows:

1. An optoacoustic spectroscopy apparatus having a fast response time to constituent changes in a flowing or stationary gas comprising a resonant chamber dimensioned to have a fundamental acoustic resonance frequency below 10 kHz, an absorption cell having dimensions substantially smaller than the resonant chamber and acoustically coupled to the resonant chamber, the absorption cell having inlet and outlet ports to accommodate the flow of gas therethrough, means for irradiating the absorption cell contents with periodic pulses of radiation absorbed by a constituent of the gas to produce corresponding pressure variations in the cell, the radiation being pulsed at a resonant frequency of the resonant chamber whereby pressure oscillations at said resonant frequency are produced in the absorption cell and coupled to the resonant chamber where corresponding pressure oscillations of increased magnitude are induced, and means coupled with the resonant chamber to measure the pressure oscillations therein and produce an electrical output which is a measure of the radiation absorbing constituent in the absorption chamber.

* * * * *